United States Patent
Cazalis et al.

(10) Patent No.: US 11,377,690 B2
(45) Date of Patent: Jul. 5, 2022

(54) METHOD AND KIT FOR MAKING AN IN VITRO PROGNOSIS OF SEVERITY FOR A PATIENT IN SEPTIC SHOCK

(71) Applicants: BIOMERIEUX, Marcy L'Etoile (FR); HOSPICES CIVILS DE LYON, Lyons (FR)

(72) Inventors: Marie-Angelique Cazalis, Vaulx en Velin (FR); Maud Tournoud, Grenoble (FR); Fabienne Venet, Lyons (FR); Alain Lepape, Saint Genis Laval (FR); Guillaume Monneret, Lyons (FR)

(73) Assignees: BIOMERIEUX, Marcy l'Etoile (FR); HOSPICES CIVILS DE LYON, Lyons (FR)

( * ) Notice: Subject to any disclaimer, the term of this patent is extended or adjusted under 35 U.S.C. 154(b) by 104 days.

(21) Appl. No.: 14/649,803

(22) PCT Filed: Jan. 10, 2014

(86) PCT No.: PCT/FR2014/050039
§ 371 (c)(1),
(2) Date: Jun. 4, 2015

(87) PCT Pub. No.: WO2014/108646
PCT Pub. Date: Jul. 17, 2014

(65) Prior Publication Data
US 2016/0017423 A1    Jan. 21, 2016

(30) Foreign Application Priority Data
Jan. 11, 2013 (FR) ........................................ 1350252

(51) Int. Cl.
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/118* (2013.01); *C12Q 2600/158* (2013.01); *G01N 2800/26* (2013.01)

(58) Field of Classification Search
CPC ............ C12Q 1/6883; C12Q 2600/118; C12Q 2600/158; G01N 33/6893; G01N 2800/26
See application file for complete search history.

(56) References Cited

U.S. PATENT DOCUMENTS

| 5,399,491 | A | 3/1995 | Kacian et al. |
| 2004/0241167 | A1 | 12/2004 | Suciu-Foca et al. |
| 2009/0203534 | A1* | 8/2009 | Hossain ............... C12Q 1/6883 506/9 |
| 2012/0077767 | A1* | 3/2012 | Zaas .................... C12Q 1/6883 514/31 |

FOREIGN PATENT DOCUMENTS

| WO | 90/06995 A1 | 6/1990 |
| WO | 91/19812 A1 | 12/1991 |
| WO | 94/12670 A2 | 6/1994 |
| WO | 2004/087949 A2 | 10/2004 |
| WO | 2008/143890 A2 | 11/2008 |

OTHER PUBLICATIONS

Nguyen (Annals of Emergency Medicine (2006) vol. 48, pp. 28-55).*
DeForge et al (Biochemcial and Biophysical research Communications (1991) vol. 174, pp. 18-24.).*
Brown et al (BMC immunology (2009) vol. 10, pp. 1-9).*
Huyhn (Rhuematology (2007) vol. 46, pp. 742-751).*
Annane (Br J Clin Pharmacology (1998) vol. 46, pp. 589-597).*
Cazalis (26th ESICM Annual Congress—Paris France—Oct. 5-9, 2013, abstract 03191).*
Pachot (Immunology (2006) vol. 106, pp. 63-71).*
Venet (Shock (2010) vol. 34, pp. 358-363).*
McIntire (Reproductive Sciences (2008) vol. 15, pp. 437-447).*
HG-U133A:210146_X_AT (https://www.affymetrix.com/analysis/netaffx/fullrecord.affx?pk=HG-U133A:210146_X_AT, downloaded Aug. 21, 2019).*
Brown (BMC Immunology (2009) vol. 10:56, pp. 1-9).*
Kamishikiryo (Current Pharmaceutical Design (2009) vol. 15, pp. 3318-3324).*
McIntire (Placenta (2008) vol. 29, pp. 631-638).*
Bustin et al., "Quantification of mRNA using real-time reverse transcription PCR (RT-PCR): trends and problems," Journal of Molecular Endocrinology, 2002, vol. 29, pp. 23-39.
Giulietti et al., "An Overview of Real-Time Quantitative PCR: Applications to Quantify Cytokine Gene Expression." Methods, 2001, vol. 25, pp. 386-401.
Hellemans et al., "qBase relative quantification framework and software for management and automated analyis of real-time quantitative PCR data," Genome Biology, 8(R19), 2007.
Lepin et al., "Functional Characterization of HLA-F and binding of HLA-F tetramers to ILT2 and ILT4 Receptors," Eur. J. Immunology., 2000, vol. 30, pp. 3552-3561.
Wong et al., "Genomic Expression Profiling Across the Pediatric Systemic Inflammatory Response Syndrome, Sepsis, and Septic Shock Spectrum," Critical care Med., 2009, vol. 37(5), pp. 1558-1566.

(Continued)

*Primary Examiner* — Steven Pohnert
(74) *Attorney, Agent, or Firm* — Oliff PLC (57) ABSTRACT

The subject of the invention is a method for making an in vitro prognosis of severity for a patient in septic shock, including the following steps: (i) the level of expression of the expression product of at least one gene chosen from the lilrb2 and lilrb1 genes is measured in vitro on the basis of a biological sample taken from the patient, (ii) the level of expression of the expression product of the at least one gene is compared with a control level of expression, of the expression product of the same gene, with a good prognosis of severity, in which a level of expression of the expression product of the at least one gene below the control level of expression indicates a poor prognosis of severity for the patient, and also a kit for implementing the method.

37 Claims, 4 Drawing Sheets
Specification includes a Sequence Listing.

(56) References Cited

OTHER PUBLICATIONS

Shanley et al., "Genome-Level Longitudinal Expression of Signaling Pathways and Gene Networks in Pediatric Septic Shock," Mol Med, 2007, vol. 13(9-10), pp. 495-508.
Wong, "Clinical Review: Sepsis and Septic Shock—the Potential of Gene Arrays," Critical Care, 2012, vol. 16:204, pp. 1-8.
Apr. 8, 2014 Written Opinion in International Patent Application No. PCT/FR2014/050039.
Apr. 8, 2014 International Search Report issued in International Patent Application No. PCT/FR2014/050039.

\* cited by examiner

METHOD AND KIT FOR MAKING AN IN VITRO PROGNOSIS OF SEVERITY FOR A PATIENT IN SEPTIC SHOCK

The present invention relates to a method and a kit for making an in vitro prognosis of severity for a patient in septic shock.

Septic syndromes represent one of the primary causes of mortality in intensive care units. They may result from a bacterial, viral, fungal or parasitic infection. They are defined as a Systemic Inflammatory Response Syndrome or SIRS;
- sepsis is a systemic inflammatory response syndrome related to an infection,
- severe sepsis is sepsis combined with arterial hypotension and/or hypoperfusion and/or dysfunction of at least one organ,
- septic shock is severe sepsis combined with persistent hypotension despite appropriate volume expanders and vasopressive treatments.

The difference between sepsis, severe sepsis and septic shock lies mainly in the extent to which all the vital functions are disrupted.

Septic syndromes have long been considered solely as an unregulated inflammatory response leading, in response to initial bacterial dissemination, to multiple organ failure of the organism. However, the failures which have been experienced in recent times of the predominantly anti-inflammatory therapeutic approaches, and also the difficulty in characterizing the high degree of heterogeneity among septic patients, have contributed to a questioning of the essentially pro-inflammatory view of the physiopathology of septic syndromes.

Currently, the immune response during septic shock is generally described in two successive phases. After a brief, highly inflammatory initial phase, which is responsible for the symptomatology of the shock proper, there is the onset of a state of immunosuppression, induced by the immunosuppressive mechanisms responsible for controlling the pro-inflammatory response. Thus, this anti-inflammatory component of the reaction to infection, initially perceived as purely compensatory, has proven to be predominant in the majority of patients and is accompanied by immunosuppression and pronounced cell hyporeactivity. Moreover, it appears that mortality mainly occurs remotely from the shock (or from the initial organ failure) in a context in which all the patients have biological symptoms of immunodeficiency.

Some markers have thus been described in the literature as being able to aid prognosis of mortality or survival for patients in septic shock. However, in all the methods described until now, blood samples are taken for the first time in the first 24 to 72 hours following the onset of shock (D1-D3), then at a later stage during the septic shock. Despite their benefit, the significance of these markers is only revealed, at the earliest, at D1-D3. In other words, they are not early enough for highly reactive treatment which is as quick as possible for a patient in shock. Yet, suitable treatment of the patient as soon as possible after shock is indispensable. It is therefore necessary, and very important, to have markers which enable this window for prognosis to be reduced as far as possible.

Completely unexpectedly, the present inventors have shown that the expression products of the lilrb2 and/or lilrb1 genes allow a prognosis of severity or of survival/mortality to be made for patients in septic shock right from the very first hours, and no later than in the first 12 hours, after the onset of shock. These genes belong to the family of immunoglobulin-like receptors which are located at chromosomal region 19q13.4.

There are several variants of the two target genes which are all relevant within the context of the invention. These variants are listed in Genbank under the following references and accession numbers:

LILRB2:
"*Homo sapiens* leukocyte immunoglobulin-like receptor, subfamily B (with TM and ITIM domains), member 2 (LILRB2), transcript"

| NM_005874.3 | variant 1 Refseq |
| NM_001080978.2 | variant 2 Refseq |

LILRB1
"*Homo sapiens* leukocyte immunoglobulin-like receptor, subfamily B (with TM and ITIM domains), member 1 (LILRB1), transcript"

| NM_006669.3 | variant 1 Refseq |
| NM_001081637.1 | variant 2 Refseq |
| NM_001081638.1 | variant 3 Refseq |
| NM_001081639.1 | variant 4 Refseq |

Thus, one subject of the present invention is a method for making an in vitro prognosis of severity (of survival or of increased risk of mortality) for a patient in septic shock, comprising the following steps:
(i) the level of expression of the expression product of at least one gene chosen from the lilrb2 and lilrb1 genes is measured in vitro on the basis of a biological sample taken from said patient,
(ii) the level of expression of the expression product of said at least one gene is compared with a control level of expression, of the expression product of the same gene, with a good prognosis of severity, in which a level of expression of the expression product of said at least one gene below said control level of expression indicates a poor prognosis of severity for the patient.

In one preferred embodiment, (i) the level of expression of the expression product of the lilrb2 gene is measured, (ii) the level of expression of the expression product of the lilrb2 gene is compared with the control level of expression, with a good prognosis, of the lilrb2 gene,
in which a level of expression of the expression product of the lilrb2 gene in the patient below that of the control level of expression indicates a poor prognosis for the patient.
In another embodiment, (i) the patient's level of expression of the expression product of the lilrb2 gene and the patient's level of expression of the expression product of the lilrb1 gene are measured, (ii) the patient's level of expression of the expression product of the lilrb2 gene and of the lilrb1 gene are compared respectively with the control level of expression of each gene, in which a level of expression of the expression product of the lilrb2 gene and of the lilrb1 gene in the patient respectively below the control level of expression of each gene indicates a poor prognosis for the patient.

The biological sample is chosen from blood, plasma, serum, saliva, urine, cerebrospinal fluid, pleural fluid and peritoneal fluid.

The method of the invention can also comprise an additional step according to which, in the step, the peripheral blood mononuclear cells (PBMCs) are extracted from the blood sample, and the subsequent steps are performed on said blood mononuclear cells, as described previously.

The expression product of the gene or genes is either an RNA, and preferably a messenger RNA, or else a cDNA, or a protein or a polypeptide. When the expression product is an RNA, its level of expression is determined by means of at least one hybridization probe specific for the expression product and preferably by means of at least two or even three hybridization probes and in particular by quantitative enzymatic amplification. When the expression product of the gene or genes is a polypeptide or a protein, its level of expression is preferably determined by a quantitative immunoassay.

Another subject of the invention is a method for carrying out in vitro monitoring of a patient in septic shock, by measuring the change in the level of expression of the expression product of at least one gene chosen from the lilrb2 and lilrb1 genes in said patient, in which (i) the level of expression of said at least one gene in a sample taken from the patient on D1 is measured, that is to say at the latest in the first 12 hours of septic shock, (ii) the level of expression of said at least one gene in a sample taken from the patient on Dx is measured, that is to say subsequently to D1, in which an increase in said level of expression of said at least one gene between D1 and Dx indicates that the patient is moving towards a good prognosis of severity.

Of course, step (ii) can be carried out several times to monitor the change in the level of expression of said at least one gene over time.

As described above, the level of expression of the expression product is preferably measured by quantitative amplification and by quantitative immunoassay.

The invention also relates to a kit for carrying out the methods described above, comprising at least one hybridization probe specific for the RNA or cDNA expression product of at least one gene chosen from the lilrb2 and lilrb1 genes or at least one specific ligand of the polypeptide or protein expression product of at least one gene chosen from the lilrb2 and lilrb1 genes, in particular an antibody or an antibody derivative or an antibody analogue.

Definitions

Biological sample means blood, plasma, serum, saliva, urine, cerebrospinal fluid, pleural fluid and peritoneal fluid.

Blood sample means either whole blood, serum or plasma.

The term expression product of a gene is intended to mean the messenger RNA or an mRNA fragment, the cDNA or a cDNA fragment, a polypeptide or a protein or a polypeptide or protein fragment.

The term specific reagent is intended to mean a reagent which reacts with biological material from the blood sample or the peripheral blood mononuclear cells (PBMCs) in order to directly or indirectly highlight the expression of a target gene, which can be determined by analysing the mRNA resulting from this gene, or by analysing the protein encoded by this gene.

By way of indication, when it is desired to determine the expression of a target gene by analysing the protein encoded by this gene, this specific reagent comprises at least one antibody specific for the protein encoded by this target gene.

By way of indication, when it is desired to determine the expression of a target gene by analysing the mRNAs transcribed from this gene, this specific reagent comprises at least one amplification primer specific for the complementary DNA of this mRNA (this is then referred to as target-gene-specific amplification primer). The complementary DNA of an mRNA may be obtained according to a protocol well known to those skilled in the art. For example, the total RNAs (comprising the ribosomal RNAs, the transfer RNAs and the mRNAs) are extracted from the blood sample or the PBMCs. A reverse transcription reaction is then carried out using a reverse transcriptase enzyme which makes it possible to obtain, from an RNA fragment, a complementary DNA (cDNA) fragment. The execution of such a step is well known to those skilled in the art. When it is desired more particularly to obtain only the complementary DNAs of the messenger RNAs, this enzymatic step is carried out in the presence of nucleotide fragments comprising only thymine bases (polyT), which hybridize via complementarity to the polyA sequence of the various mRNAs so as to form a polyT-polyA complex which then serves as the starting point for the reverse transcription reaction carried out by the reverse transcriptase enzyme. Various complementary DNAs of the various messenger RNAs initially present in the blood sample or in the PBMCs are then obtained. Hereinafter, the term cDNA denotes a complementary DNA of a messenger RNA.

The term amplification primer is intended to mean a nucleotide fragment comprising from 5 to 100 nucleotide units, preferably from 15 to 25 nucleotide units, and having a specificity of hybridization under given conditions for the initiation of an enzymatic polymerization, for example in an enzymatic amplification reaction.

The term enzymatic amplification reaction is intended to mean a process which generates multiple copies of a target nucleotide fragment by means of specific amplification primers through the action of at least one enzyme. Such amplification reactions are well known to those skilled in the art and mention can notably be made of the following techniques: PCR (Polymerase Chain Reaction), LCR (Ligase Chain Reaction), RCR (Repair Chain Reaction), 3SR (Self Sustained Sequence Replication) with patent application WO-A-90/06995, NASBA (Nucleic Acid Sequence-Based Amplification) and TMA (Transcription Mediated Amplification) with U.S. Pat. No. 5,399,491.

The term amplicons is then used to denote the polynucleotides generated by an enzymatic amplification technique. Preferably, when the enzymatic amplification is a PCR, the specific reagent comprises at least 2 specific amplification primers in order to amplify a particular region of the complementary DNA of the mRNA resulting from the target gene. When the enzymatic amplification is a PCR carried out after a reverse transcription reaction, this is referred to as RT-PCR.

The term hybridization probe is intended to mean a nucleotide fragment comprising from 5 to 100 nucleotide units, notably from 6 to 35 nucleotide units, having a specificity of hybridization under given conditions for forming a hybridization complex with a target nucleotide fragment. In the present invention, the target nucleotide fragment can be a nucleotide sequence included in a messenger RNA or a nucleotide sequence included in a complementary DNA obtained by reverse transcription of said messenger RNA.

The term hybridization is intended to mean the process during which, under suitable conditions, two nucleotide fragments, such as, for example, a hybridization probe and a target nucleotide fragment, having sufficiently complementary sequences, are capable of forming a double strand with stable and specific hydrogen bonds. A nucleotide fragment "capable of hybridizing" with a polynucleotide is a fragment that can hybridize with said polynucleotide under hybridization conditions which can be determined in each case in a known manner. The hybridization conditions are determined by the stringency, that is to say the rigour of the operation conditions. The higher the stringency at which the hybridization is carried out, the more specific said hybridization is. The stringency is defined notably according to the base composition of a probe/target duplex, and also by the degree of mismatch between two nucleic acids. The stringency may also depend on the reaction parameters, such as the concentration and the type of ionic species present in the hybridization solution, the nature and the concentration of denaturing agents and/or the hybridization temperature. The stringency of the conditions under which a hybridization reaction should be carried out will depend mainly on the hybridization probes used. All these data are well known and the appropriate conditions may be determined by those skilled in the art. In general, depending on the length of the hybridization probes used, the temperature for the hybridization reaction is between about 20 and 70° C., in particular between 35 and 65° C. in a saline solution at a concentration of about 0.5 to 1 M. A step of detecting the hybridization reaction is then carried out.

The term detection is intended to mean either a direct detection by means of a physical method, or a method of detection using a label. Numerous detections methods are available for detecting nucleic acids [1, 2].

The term label is intended to mean a tracer capable of generating a signal. A nonlimiting list of these tracers includes enzymes which produce a signal that is detectable, for example, by colorimetry, fluorescence or luminescence, such as horseradish peroxidase, alkaline phosphatase, β-galactosidase, glucose-6-phosphate dehydrogenase; chromophores such as fluorescent, luminescent or colouring compounds; electron-dense groups that are detectable by electron microscopy or by their electrical properties, such as conductivity, by amperometry or voltammetry methods, or by impedance measurements; groups that are detectable by optical methods such as diffraction, surface plasmon resonance or variation of contact angle or by physical methods such as atomic force spectroscopy, tunnel effect, etc.; radioactive molecules such as $^{32}P$, $^{35}S$ or $^{125}I$. Thus, the polynucleotide may be labelled during the enzymatic amplification step, for example using a labelled nucleotide triphosphate for the amplification reaction. The labelled nucleotide will be a deoxyribonucleotide in amplification systems generating a DNA, such as PCR, or a ribonucleotide in amplification techniques generating an RNA, such as the TMA or NASBA techniques. The polynucleotide can also be labelled after the amplification step, for example by hybridizing a probe that is labelled according to the sandwich hybridization technique described in document WO-A-91/19812.

Within the context of the present invention, the hybridization probe can be a "capture" probe. In this case, the target nucleotide fragment can be pre-labelled by means of a label. The "capture" probe is immobilized or immobilizable on a solid support by any appropriate means, that is to say directly or indirectly, for example by covalence or adsorption. A hybridization reaction is then carried out between said detection probe and the labelled target nucleotide fragment.

The hybridization probe can also be a "detection" probe. In this case, the hybridization probe can be labelled by means of a label. A hybridization reaction is then carried out between said capture probe and the target nucleotide fragment.

Regardless of whether a "capture" probe or a "detection" probe is used, the hybridization reaction can be carried out on a solid support which includes all the materials on which a nucleic acid can be immobilized. Synthetic materials or natural materials, which have optionally been chemically modified, can be used as solid support, notably polysaccharides, such as cellulose-based materials, for example paper, cellulose derivatives such as cellulose acetate and nitrocellulose or dextran, polymers, copolymers, notably based on monomers of the styrene type, natural fibres such as cotton, and synthetic fibres such as nylon; mineral materials such as silica, quartz, glasses or ceramics; latices; magnetic particles; metal derivatives, gels, etc. The solid support can be in the form of a microtitration plate, a membrane as described in application WO-A-94/12670, a particle or a biochip.

In the present invention, the determination of the expression of a target gene can be analyzed by the expression of the mRNAs which are transcribed at a given time. In this case, the biological material is a nucleic acid, and the specific reagent can be, without preference, an amplification primer or a hybridization probe which are as defined above.

The expression of a target gene can be determined as follows:

1) after having extracted the total RNAs from a blood sample or PBMC sample, a reverse transcription step is carried out, as described above, in order to obtain the various complementary DNAs of the various messenger RNAs initially present in the blood sample or the PBMCs (or cDNAs);

2) the cDNAs are specifically amplified. In this case, the specific reagent used comprises at least one amplification primer specific for the target gene, as defined above. This step can be carried out notably by means of an amplification reaction of PCR type or by means of any other suitable amplification technique;

3) the expression of the target gene is determined by quantifying the cDNAs. The cDNAs can be quantified in particular by using a quantification range obtained by means of an amplification reaction carried out to saturation. In order to take into account the variability of the enzymatic efficiency that can be observed during the various steps (reverse transcription, quantitative PCR, etc.), the expression of the target gene of the various groups of patients can be standardized by simultaneous determination of the expression of a "reference" gene, the expression of which is similar in the various groups of patients. By calculating the ratio between the expression of the target gene and the expression of the reference gene, any variability between the various experiments is thus corrected. Those skilled in the art can notably refer to the following publications: [3-4] Bustin S A *Journal of Molecular Endocrinology,* 2002, 29: 23-39; Giulietti A *Methods,* 2001, 25: 386-401.

The expression of a target gene can also be determined as follows:

1) after having extracted the total RNAs from a blood or PBMC sample, a reverse transcription step is carried out, as described above, in order to obtain the various complementary DNAs of the various messenger RNAs initially present in the sample or the PBMCs (or cDNAs);

2) the cDNAs are immobilized on a membrane;

3) the expression of the target gene is determined by hybridizing the cDNAs to pre-labelled hybridization probes specific for the target gene. Such hybridization techniques are well known to those skilled in the art, and mention can notably be made of the Northern blotting technique. This hybridization reaction can be carried out after a step of specific amplification of the complementary DNAs of the messenger RNAs of a target gene when, notably, the gene is weakly expressed.

The expression of a target gene can also be analyzed by the expression of the proteins encoded by the target gene. In this case, the biological material is a protein or a polypeptide and several detection techniques with or without ligand can be used. Mass spectrometry can be used as a technique for detection without a ligand. The specific reagent can be a ligand specific for the protein encoded by the target gene, for a system of detection with a ligand.

In particular, the ligand is an antibody or an antibody derivative (such as an antibody fragment) or an antibody analogue.

Recombinant antibodies specific for the translated protein of the target gene can be obtained according to conventional methods known to those skilled in the art, using prokaryotic organisms, such as bacteria, or using eukaryotic organisms, such as yeasts, or mammalian, plant, insect or animal cells, or using extracellular production systems.

Monoclonal antibodies can be prepared according to the conventional techniques known to those skilled in the art, such as the hybridoma technique, the general principle of which is summarized below.

In a first step, an animal, generally a mouse (or cells in culture in the context of in vitro immunizations) is immunized with a target antigen of interest, the B lymphocytes of said animal then being capable of producing antibodies against said antigen. These antibody-producing lymphocytes are then fused with "immortal" myeloma cells (murine in the example) so as to give rise to hybridomas. Cells capable of producing a particular antibody and of multiplying indefinitely are then selected from the heterogeneous mixture of the cells thus obtained. Each hybridoma is multiplied in the form of a clone, each one resulting in the production of a monoclonal antibody of which the recognition properties with respect to the antigen of interest may be tested for example by ELISA, by one-dimensional or two-dimensional immunoblotting, by immunofluorescence, or by means of a biosensor. The monoclonal antibodies thus selected are subsequently purified, notably according to the affinity chromatography technique.

Antibody fragments may, for example, be obtained by proteolysis. Thus, they may be obtained by enzymatic digestion, resulting in fragments of Fab type (treatment with papain [5]) or of F(ab)'2 type (treatment with pepsin [6]). They may also be prepared by a recombinant route [7]. Another antibody fragment which is suitable for the purposes of the invention comprises an Fv fragment, which is a dimer consisting of the noncovalent combination of the variable light (VL) domain and the variable heavy (VH) domain of the Fab fragment, therefore of the combination of two polypeptide chains. In order to improve the stability of the Fv fragment due to dissociation of the two polypeptide chains, this Fv fragment can be modified by genetic engineering by inserting a suitable peptide linker between the VL domain and the VH domain [8]. This is then called an scFv fragment ("single chain. Fragment variable") since it consists of a single polypeptide chain. The use of a peptide linker composed preferentially of 15 to 25 amino acids makes it possible to link the C-terminal end of one domain to the N-terminal end of the other domain, thus constituting a monomeric molecule which has binding properties similar to those of the antibody in its complete form. Both orientations of the VL and VH domains are suitable (VL-linker-VH and VH-linker-VL) since they have identical functional properties. Of course, any fragment known to those skilled in the art having the immunological characteristics defined above is suitable for the purposes of the invention.

The term antibody analogue is intended in particular to mean affinity proteins with competitive properties (Nanofitins™)

When the biological material is a polypeptide or protein resulting from the expression of a gene, the expression of the latter can be determined by detecting and/or quantifying said protein by Western blotting or ELISA, or any other method known to those skilled in the art, such as a method of chemiluminescence based on the biological material.

The ELISA ("Enzyme Linked ImmunoSorbent Assay") technique is an immunoenzymatic assay on a solid support. This assay falls within the more general context of EIAs ("Enzyme Immunoassays") in which the assay is coupled to a reaction catalyzed by an enzyme. The technique uses one or two antibodies. The antibody for detecting the formation of immune (antigen/antibody) complexes is coupled to the enzyme and can generate the emission of a signal by a chromogenic or fluorogenic substrate.

The Western blotting technique is an assay for detecting a specific protein in a sample by means of an antibody specific for this protein, comprising the following steps as described below.

The first step is gel electrophoresis, which makes it possible to separate the proteins in the sample according to their size.

The proteins in the gel are then transferred onto a membrane (nitrocellulose, PVDF, etc.) by pressure or by application of an electric current, the proteins binding to the membrane by virtue of hydrophobic and ionic interactions. After saturation of the nonspecific interaction sites, a first antibody, specific for the protein to be studied (primary antibody), is incubated with the membrane.

The membrane is then rinsed in order to remove the unbound primary antibodies, and then incubated with "secondary" antibodies, which will bind to the primary antibodies. This secondary antibody is usually bound to an enzyme which allows visual identification of the protein studied on the membrane. The addition of a labelled substrate for the enzyme produces a coloured reaction which is visible on the membrane.

FIGURES

FIG. 1.

FIG. 2.

FIG. 3.

FIG. 4.

FIG. 5.

FIG. 6.

FIG. 7.

FIG. 8.

FIG. 9.

EXAMPLES

Finding an Expression Profile for the Prognosis of Survival or Severity for a Patient in Septic Shock Example 1

Description of the Patients 1.1 Discovery Cohort

The study was carried out on a cohort of 51 patients in septic shock, aged from 25 to 85 years (33 males, 18 females, median age: 66 years) who were admitted to the intensive care unit of the Centre Hospitalier Lyons Sud—Lyons (France) between 2004 and 2009 for treatment for septic shock. Their characteristics are given in Table 1 below. All the patients were in septic shock requiring treatment with amines after volume expander treatment. The start of treatment with catecholamines was taken as T0 for the septic shock and the study. Among the 51 patients of the cohort, patients (33%) died in the first 28 days after beginning catecholamine treatment (non-surviving patients: NS) and 34 patients survived beyond 28 days (surviving patients: S). Patients aged under 18 were excluded from the study.

The severity of the illness was calculated by the SAPS II score (Simplified Acute Physiology Score) established by Le Gall et al. in 1993, which takes into account various clinical parameters (age, heart rate, core temperature, $PaO_2/FiO_2$, diuresis, blood urea, leukocytes, kalaemia, natraemia, blood bicarbonate level, bilirubin, type of admission, associated pathological conditions and the Glasgow coma scale) and also the SOFA score (Sequential Organ Failure Assessment score) which takes into account organ failures (based on six different grades, one for each of respiratory, cardiovascular and hepatic pathways, coagulation, and renal and neurological systems). These scores are inversely proportional to survival. For the group of patients studied, the median SAPS II is 51 and the median SOFA is 10. All this information is summarized in Table 1 below.

TABLE 1

|  |  | Non-surviving n = 17 (33%) | Surviving n = 34 (67%) | Total n = 51 (%) | P-value |
|---|---|---|---|---|---|
| Female n (%) |  | 9 (53) | 9 (26) | 18 (35) | 0.062 |
| Male n (%) |  | 8 (47) | 25 (74) | 33 (65) |  |
| Median age (years) (Q1-Q3) |  | 59 (48-70) | 66 (56-76) | 66 (54-74) | 0.418 |
| Median SAPS II (Q1-Q3) |  | 64 (56-70) | 47 (38-55) | 51 (43-61) | <.001 |
| Median SOFA (Q1-Q3) |  | 12 (10-15) | 9 (8-11) | 10 (8-12) | 0.002 |
| Type of infection | Community-acquired n (%) | 8 (47) | 17 (50) | 25 (49) | ns |
|  | nosocomial n (%) | 8 (47) | 17 (50) | 25 (49) |  |
| Site of infection | abdominal n (%) | 4 (38) | 15 (40) | 19 (39) | 0.291 |
|  | pulmonary n (%) | 10 (46) | 13 (40) | 23 (42) |  |
|  | others n (%) | 4 (16) | 6 (20) | 10 (19) |  |

1.2 Control Series

Healthy volunteer subjects (HS) were recruited in order to obtain a control series, the samples of which were processed and analyzed under conditions identical to those of the patients. There were 24 healthy subjects (12 females and 12 males) with a median age of 57 years. This information is summarized in Table 2 below.

TABLE 2

|  | HS n = 24 (%) |
|---|---|
| Female n (%) | 12 (50) |
| Male n (%) | 12 (50) |
| Median age (years) (Q1-Q3) | 57 (52-60) |

1.3 Validation Cohort:

The validation cohort includes 262 patients in septic shock, from to 93 years of age (164 males, 93 females, median age: 67 years) who were admitted to 6 intensive care units in Lyons (France) between 2009 and 2011 for treatment for septic shock. These patients were all in a state of shock requiring treatment with amines after volume expander treatment. The start of treatment with catecholamines was taken as T0 for the septic shock. Of the 262 patients included in the study, 90 of them (34%) died in the first 28 days after beginning catecholamine treatment. Patients aged under 18 were excluded from the study.

The severity of the illness was calculated by the SAPS-II score and the SOFA score. For the group of patients studied, the median SAPS II is 62 and the median SOFA is 12.

Table 3 below summarizes the information on the patients from the validation cohort.

TABLE 3

|  | Non-surviving n = 90 (34%) | Surviving n = 172 (66%) | Total n = 262 (%) | P-value |
|---|---|---|---|---|
| Female n (%) | 33 (36.7) | 65 (37.8) | 98 (37.4) | 0.965 |
| Male n (%) | 57 (63.3) | 107 (62.2) | 164 (62.6) |  |
| Median age (years) (Q1-Q3) | 71.5 (63-78) | 65 (56-77) | 67 (58-78) | 0.003 |
| Median SAPS II (Q1-Q3) | 77 (63-93) | 57 (44-68) | 62 (50-77) | <.001 |
| Median SOFA (Q1-Q3) | 14 (12-16) | 11 (9-13) | 12 (10-14) | <.001 |

TABLE 3-continued

|  |  | Non-surviving n = 90 (34%) | Surviving n = 172 (66%) | Total n = 262 (%) | P-value |
|---|---|---|---|---|---|
| Type of infection | Community-acquired n (%) | 48 (53.3) | 114 (66.3) | 162 (61.8) | 0.041 |
|  | nosocomial n (%) | 42 (46.7) | 58 (33.7) | 100 (38.2) |  |
| Site of infection | abdominal n (%) | 30 (33.3) | 41 (23.8) | 71 (27.1) | 0.212 |
|  | pulmonary n (%) | 36 (40.0) | 72 (41.9) | 108 (41.2) |  |
|  | others n (%) | 24 (26.7) | 59 (34.3) | 83 (31.7) |  |

Example 2

Sampling and Data Collection

The first blood samples were obtained at the latest 12 hours after the onset of septic shock.

2.1 Extraction of Total RNAs from the Biological Sample:

The samples were collected directly in PAXgene™ Blood RNA tubes (PreAnalytix, Hilden, Germany). After sampling, the tubes were left at room temperature for 4 hours and then stored at −80° C. until the biological material was extracted, with the aim of optimizing and standardizing the sample storage conditions. More precisely, in this protocol, the total RNAs were extracted by means of PAXgene™ Blood RNA® kits (PreAnalytix), following the manufacturer's instructions.

The quality of the extracted total RNAs was analyzed using the AGILENT 2100 bioanalyser (Agilent Technologies, Waldbronn, Germany) by means of the Lab-on-chip RNA 6000 Nano Assay system (Agilent). The total RNAs comprise the transfer RNAs, messenger RNAs (mRNAs) and ribosomal RNAs.

2.2 Discovery Study:

For the discovery study, the mRNA reverse transcription reaction was carried out according to the Affymetrix protocol using 50 ng of total RNA. An oligonucleotide primer was used to target all the RNAs during the reverse transcription. All the steps were carried out with the NuGen WTO kit and hybridized on DNA chips. The cRNA hybridization is carried out with GeneChipHuman Genome U133 Plus 2 biochips before the step of signal amplification by incubating with the SAPE mixture containing Streptavidin-phycoerythrin then goat anti-Streptavidin IgG antibodies mixed with biotinylated anti-goat IgG antibody. This last step uses the Fluidic FS450 station. Analysis of the Affymetrix data starts with capturing the image of the biochip using the GeneChip® 3000 scanner from Affymetrix. The data are then normalized by RMA (Robust Multi-array Average). All the data based on signal intensity are used after normalization. The differences in the levels of mRNA expression between the patients who died in the first 28 days (non-surviving patients) and the surviving patients are determined by the SAM method (Tusher, Tibshirani and Chu, 2001).

Figure 1:
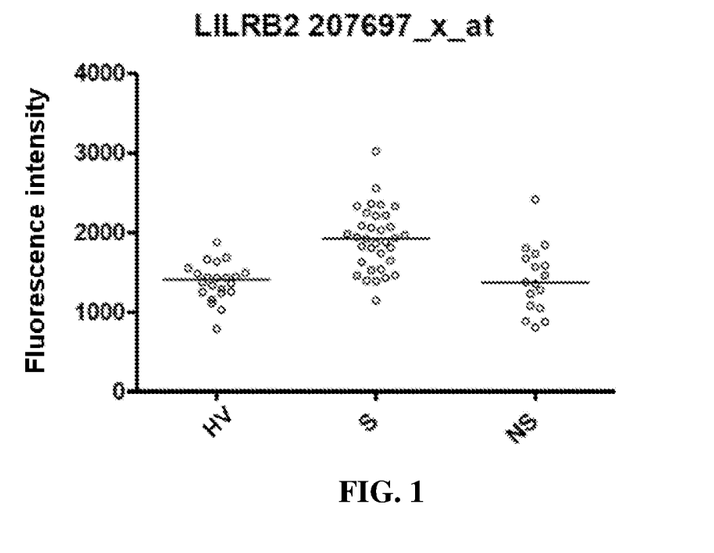
FIG. 1 shows the level of expression of LILRB2 with Affymetrix probeset: 207967_x_at. The data is expressed in terms of fluorescence intensity for the 3 groups of patients: healthy volunteers (HV), non-surviving patients (NS) and surviving patients (S).
Figure 2:
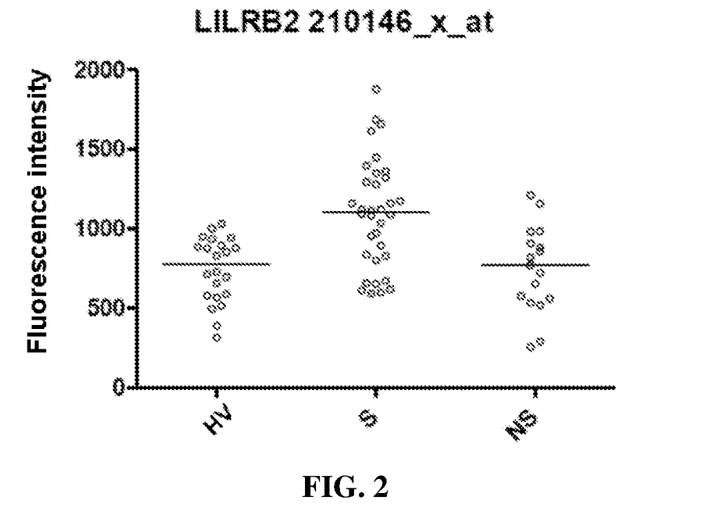
FIG. 2 shows the level of expression of LILRB2 with Affymetrix probeset: 210146_x_at. The data is expressed in terms of fluorescence intensity for the 3 groups of patients: healthy volunteers (HV), non-surviving patients (NS) and surviving patients (S).

Among the genes expressed differentially between surviving patients, non-surviving patients and healthy controls, an over-expression of LILRB2 was observed in the surviving patients compared to the level of expression obtained both in the healthy controls and in the non-surviving patients, both with comparable levels of expression. These results are given in appended FIGS. 1-3 independent Affymetrix probesets, identified respectively as 207697_x_at and 210146_x_at, which confirms the robustness and reliability of the results. In FIGS. 1 and 2, the data are presented as fluorescence intensity for the 2 Affymetrix probesets 207697_x_at and 210146_x_at, respectively, for the 3 groups of patients: healthy volunteers (cf. Table 2), non-surviving patients and surviving patients (cf. Table 1).

The fluorescence intensity of the probesets 207697_x_at and 210146_x_at was compared for the surviving and non-surviving patients. The results are given below.

| Probeset | SFC | AUC | p-value |
|---|---|---|---|
| 207697_x_at | 1.53 | 0.84 | 0.0002 |
| 210146_x_at | 1.19 | 0.78 | 0.0012 |

SFC: Standard Fold Change
AUC: Area Under Curve
p-value: according to the Mann-Whitney test The fluorescence intensity was then correlated for the 2 Affymetrix probesets. The results are given in FIG. 3.

Figure 3:
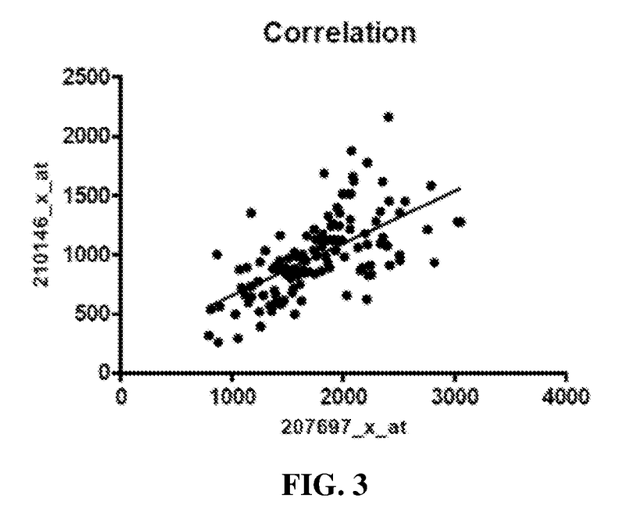
FIG. 3 shows the correlation of the fluorescence intensity for LILRB2 with the 2 Affymetrix probesets.

| Spearman correlation coefficient r | 0.68 |
|---|---|
| 95% confidence interval | 0.565 to 0.762 |
| Spearman test p value significance | <0.0001 |

As can be seen from FIG. 3, very good correlation is observed for the 2 Affymetrix probesets.

Figure 4:
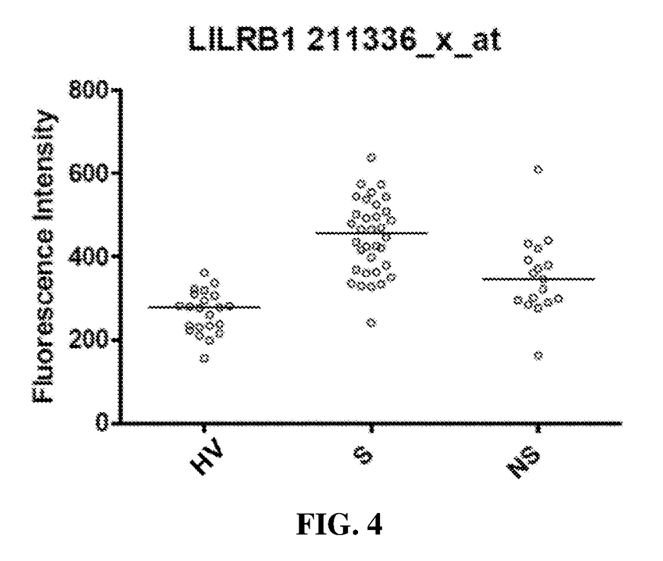
FIG. 4 shows the levels of expression of LILRB1 with the Affymetrix probeset 211336_x_at. The data are expressed in terms of fluorescence intensity for the 3 groups of patients: healthy volunteers (HV), non-surviving patients (NS) and surviving patients (S).

Of those genes expressed differentially between surviving patients, non-surviving patients and healthy controls, an over-expression of LILRB1 was also observed in the surviving patients compared to the level of expression obtained both in the healthy controls and in the non-surviving patients. These results are given in appended FIG. 4 with 1 independent Affymetrix probeset, identified respectively as 207697_x_at and 211336_x_at for the three groups of patients: healthy volunteers, non-surviving patients and surviving patients. The results are given in terms of fluorescence intensity.

Figure 5:
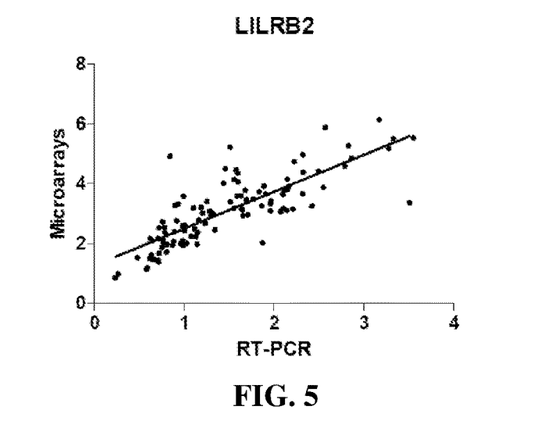
FIG. 5 shows the correlation of the fluorescence intensity between the 2 Affymetrix probesets for the LILRB1 (211336_x_at) and LILRB2 (207697_x_at) genes.

The fluorescence intensity was then correlated for the 2 Affymetrix probesets for the LILRB1 (211336_x_at) and LILRB2 (207697_x_at) genes. The results are given in FIG. 5. A significant correlation (0.86[0.81–0.90]) between the expression results for the two LILRB2 and LILRB1 genes is observed.

2.3 Technical Validation (Platform Transfer):

In order to confirm the results by means of another molecular biology technique, the LILRB2 RNA expression was measured by quantitative RT-PCR on the same cohort. Briefly, a reverse transcription (RT) reaction was carried out starting from 200 ng of total RNA in a final volume of 20 µl by means of SuperScript® VILO™ system kits (Invitrogen, Carlsbad, Calif., USA), following the manufacturer's instructions. Each cDNA solution was diluted to ¹⁄₁₀ in DEPC water. A standard was prepared for the gene of interest (LILRB2) and the reference gene (HPRT1) by PCR (polymerase chain reaction) amplification carried out to saturation. The amplicons obtained were purified (PCR purification kit, Qiagen Ltd) and the presence of a single amplicon was verified by capillary electrophoresis by means of the AGILENT 2100 bioanalyser (Agilent Technologies, Waldbronn, Germany) and the Lab-on-chip DNA Assay system (Agilent).

The LightCycler™ 480 (Roche) was used and the PCR reactions were carried out by means of the LightCycler® 480 Probes Master kit (Roche Molecular Biochemicals). Each PCR was carried out in a final volume of 20 µl containing 10 µl LightCycler® 480 Probes Master, 2× conc., 2 µl primers-probe MIX, 10× conc. containing sense and antisense primers (0.5 µM final concentration) and also the Taqman probe (0.1 µM final concentration), and 8 µl of cDNA solution diluted to one twentieth. After a 10 min denaturing step at 95° C., the amplification was carried out by means of 40 cycles of a "touch-down" PCR protocol (10 sec at 95° C., 29 sec of hybridization at 68-58° C., followed by extension for 11 sec at 72° C.). At the end of each cycle, the fluorescence given off by the Taqman hydrolysis probe was measured.

The primer combinations required for quantifying the HPRT1 reference gene and the LILRB2 gene of interest are described below. For HPRT1, the Genbank accession No. is NM_000194.2 and the amplified region is 630-788. For LILRB2, variant 1, the Genbank accession No. is NM_005874.3 and the amplified region is 2006-2182, and for variant 2, the Genbank accession No. is NM_001080978.2 and the amplified region is 1791-1879. LILRB2:

```
                                          (SEQ ID NO: 1)
5'-->3' sense primer CCAGAGCCCACAGACAGAGG (SEQ ID NO: 2)
5'-->3' antisense primer TGTCCTTCACGGCAGCATAGA (SEQ ID NO: 3)
   TaqMan probe GACTCCACACTCAGTAGAAG
```
HPRT1: 158 bp Amplicon

```
                                          (SEQ ID NO: 4)
5'-->3' sense primer CCAAAGATGGTCAAGGTCGC (SEQ ID NO: 5)
5'-->3' antisense primer GACACAAACATGATTCAAATCC (SEQ ID NO: 6)
TaqMan probe CAAGTTTGTTGTAGGATATGCCC
```

Figure 6:
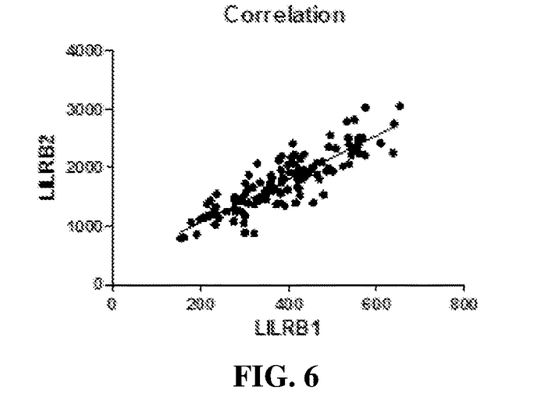
FIG. 6 shows the correlation between the fluorescence intensity of the probeset (207697_x_at) obtained with the Affymetrix platform and the LILRB2 CNRQ measurements obtained by RT-qPCR on the discovery cohort.

The amount of LILRB2 target mRNA relative to the amount of mRNA from the HPRT1 reference gene was analyzed by the relative quantification technique with LightCycler Relative Quantification Software (Roche Molecular Biochemicals). The "Second Derivative Maximum Method" of the LightCycler™ software (Roche) was used to automatically determine the crossing point (Cp) for each sample. The Cp value was defined as the number of cycles for which the fluorescence was significantly different to the background noise. Five serial ⅒ dilutions were carried out in quadruplicate with each standard in order to generate a calibration curve expressing Cp as a function of the logarithm of the copy number. The standard dilutions were optimized so that the calibration curve covered the expected level of expression for the target gene and the reference gene. The relative standard curves describing the efficiency of PCR for the target gene and the reference gene were generated and used to carry out a relative quantification called CNRQ (calibrated normalized relative quantities), described by Jan Hellemans et al. (qBase relative quantification framework and software for management and automated analysis of real-time quantitative PCR data. Genome Biology 2007). Appended FIG. 6 shows the correlation between the fluorescence intensity of the probeset (207697_x_at) obtained with the Affymetrix platform and the CNRQ measurements obtained by RT-qPCR on the discovery cohort for the LILRB2 gene. The results show a significant correlation (0.81[0.72–0.86]) between the Affymetrix results and those from quantitative RT-PCR, confirming the relevance of the gene.

| | |
|---|---|
| Spearman correlation coefficient r | 0.8075 |
| 95% Confidence interval | 0.7254 to 0.8670 |
| Spearman test p value significance | <0.0001 |

Figure 7:
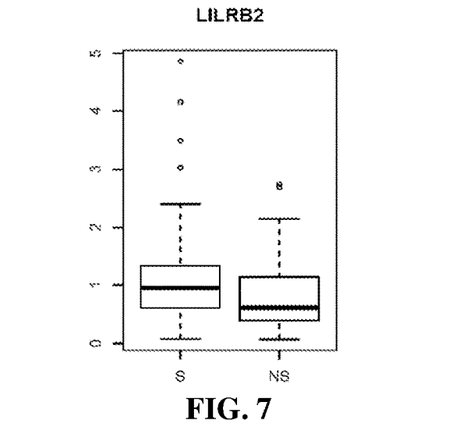
FIG. 7 gives the LILRB2 CNRQs for surviving (S) and non-surviving (NS) patients.

2.4 Biological Validation:

In order to validate the association between the expression of LILRB2 and the prediction of survival for patients in septic shock, the LILRB2 mRNA expression was measured by quantitative RT-PCR on a validation cohort including 262 patients in septic shock, with 172 surviving patients and 90 non-surviving patients (died in the first 28 days)(cf. Table 3). FIG. 7 gives the CNRQs for LILRB2 for surviving patients (S) and non-surviving patients (NS).

A logistic model was used to describe the association between LILRB2 and the probability of death. The logistic model describes the probability of dying before the $28^{th}$ day. The measurement of the association between the probability of death and the covariable is the Odds Ratio (OR). This measurement of association can be interpreted as a relative risk. For example, if OR=2 for group 1 versus group 2, this means that the probability of death for the patients from group 1 is equal to twice the probability of death for the patients from group 2.

The Odds Ratio for an increment of 1 point of the LILRB2 CNRQ is 0.47 (p=0.0028). The Odds Ratio for patients with LILRB2 CNRQ values of 1.3 ($3^{rd}$ quartile) and 0.5 ($1^{st}$ quartile) is 0.55. Thus, the patients with a high level of LILRB2 expression have a significantly lower probability of dying than patients with a lower level of expression.

Figure 8:
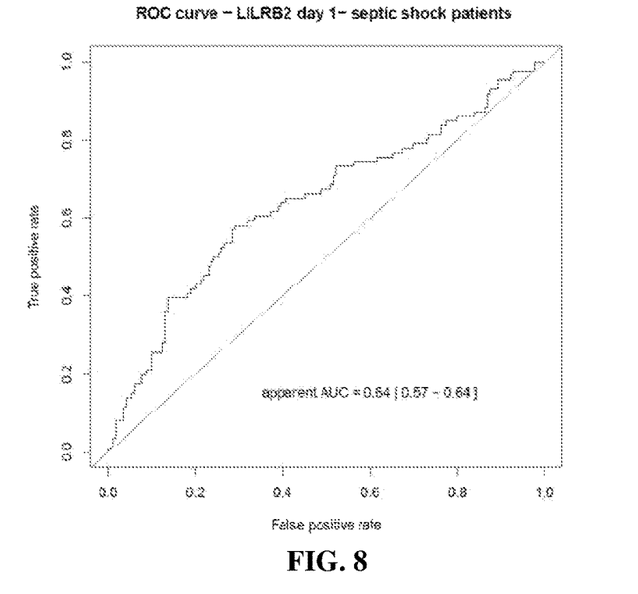
FIG. 8 shows the ROC curve for the association between the LILRB2 CNRQ values and the probability of death for patients in septic shock.

FIG. 8 shows the ROC curve of the association between the LILRB2 values and the probability of death for patients in septic shock.

Figure 9:
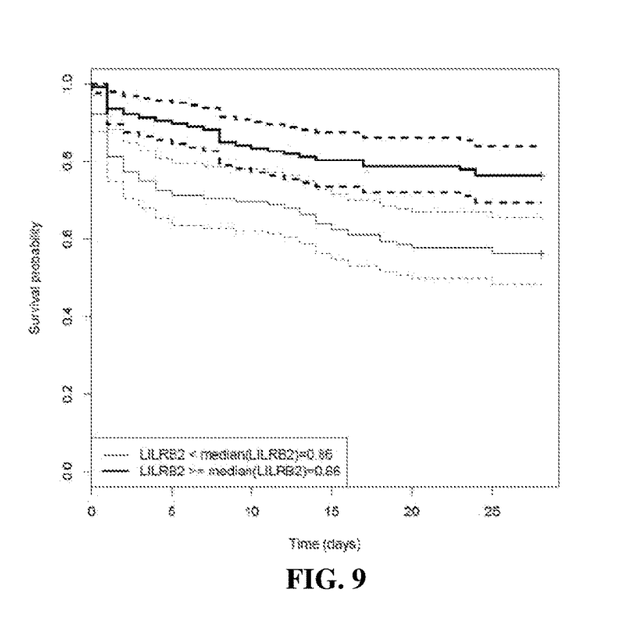
FIG. 9 shows the Kaplan-Meier survival curve for patients with LILRB2 CNRQ values above the median (0.86) in bold font and below the median in standard font.

LILRB2 is also associated with the date of survival of the patients in septic shock (and not only with the probability of death in the first 28 days). FIG. 9 shows the Kaplan-Meier survival curve for patients in septic shock at D1 with LILRB2 CNRQ values above the median (0.86) in bold font and below the median in standard font.

The invention claimed is:

1. A method of measuring gene expression for a patient in septic shock, comprising:
   obtaining a biological sample taken from the patient in septic shock within 12 hours from start of vasopressive treatment; and
   assaying the biological sample to measure an expression level of an expression product expressed from any of (i) a *Homo sapiens* leukocyte immunoglobulin-like receptor, subfamily B with transmembrane domain (TM) and immunoreceptor tyrosine-based inhibition motif (ITIM) domains, member 2 (lilrb2) gene, or (ii) a *Homo sapiens* leukocyte immunoglobulin-like receptor, subfamily B with TM and ITIM domains, member 1 (lilrb1) gene,
   wherein the expression level of the expression product is measured without hybridization on a biochip.

2. The method of claim 1, wherein the vasopressive treatment is catecholamine treatment.

3. The method of claim 1, wherein the biological sample is assayed to measure whether there is overexpression of the expression product relative to a control level from either a healthy subject or non-surviving septic-shock patient.

4. The method of claim 1, wherein the expression level of an expression product of the lilrb2 gene is measured.

5. The method of claim 1, wherein the expression level of an expression product of the lilrb1 gene is measured.

6. The method of claim 1, wherein the expression level of an expression product of the lilrb2 gene is measured and the expression level of an expression product of the lilrb1 gene is measured.

7. The method of claim 1, wherein the expression product is mRNA and cDNA is obtained from the mRNA during measurement of the expression level.

8. The method of claim 1, wherein the expression product is mRNA and the mRNA is measured using at least one hybridization probe.

9. The method of claim 1, wherein assaying the biological sample includes performing a quantitative polymerase chain reaction (PCR).

10. The method of claim 1, wherein assaying the biological sample includes performing a quantitative immunoassay.

11. The method of claim 1, further comprising:
    obtaining a later biological sample that is taken from the patient in septic shock on a later day than the biological sample that was taken within 12 hours from the start of vasopressive treatment; and
    assaying the later biological sample to measure the expression level of the expression product expressed from any of the lilrb2 gene or lilrb1 gene.

12. The method of claim 11, wherein the expression levels of an expression product of the lilrb2 gene are measured by assaying the biological samples.

13. The method of claim 11, wherein the expression levels of an expression product of the lilrb1 gene are measured by assaying the biological samples.

14. The method of claim 11, wherein the expression levels of an expression product of the lilrb2 gene are measured and the expression levels of an expression product of the lilrb1 gene are measured by assaying the biological samples.

15. A method of measuring gene expression for a patient in septic shock, comprising:
    obtaining a biological sample taken from the patient in septic shock within 12 hours from onset of septic shock, which is characterized at least by sepsis, dysfunction of at least one organ, and hypotension despite volume-expander treatment; and
    assaying the biological sample to measure an expression level of an expression product expressed from any of (i) a *Homo sapiens* leukocyte immunoglobulin-like receptor, subfamily B with transmembrane domain (TM) and immunoreceptor tyrosine-based inhibition motif (ITIM) domains, member 2 (lilrb2) gene, or (ii) a *Homo sapiens* leukocyte immunoglobulin-like receptor, subfamily B with TM and ITIM domains, member 1 (lilrb1) gene,
    wherein the expression level of the expression product is measured without hybridization on a biochip.

16. The method of claim 15, wherein the biological sample is taken from the patient within 12 hours from start of vasopressive treatment.

17. The method of claim 16, wherein the vasopressive treatment is catecholamine treatment.

18. The method of claim 15, wherein the biological sample is assayed to measure whether there is overexpression of the expression product relative to a control level from either a healthy subject or non-surviving septic-shock patient.

19. The method of claim 15, wherein the expression level of an expression product of the lilrb2 gene is measured.

20. The method of claim 15, wherein the expression level of an expression product of the lilrb1 gene is measured.

21. The method of claim 15, wherein the expression level of an expression product of the lilrb2 gene is measured and the expression level of an expression product of the lilrb1 gene is measured.

22. The method of claim 15, wherein the expression product is mRNA and cDNA is obtained from the mRNA during measurement of the expression level.

23. The method of claim 15, wherein the expression product is mRNA and the mRNA is measured using at least one hybridization probe.

24. The method of claim 15, wherein assaying the biological sample includes performing a quantitative polymerase chain reaction (PCR).

25. The method of claim 15, wherein assaying the biological sample includes performing a quantitative immunoassay.

26. The method of claim 15, further comprising:
    obtaining a later biological sample that is taken from the patient in septic shock on a later day than the biological sample that within 12 hours from the onset of septic shock; and
    assaying the later biological sample to measure the expression level of the expression product expressed from any of the lilrb2 gene or lilrb1 gene.

27. The method of claim 26, wherein the expression levels of an expression product of the lilrb2 gene are measured by assaying the biological samples.

28. The method of claim 26, wherein the expression levels of an expression product of the lilrb1 gene are measured by assaying the biological samples.

29. The method of claim 26, wherein the expression levels of an expression product of the lilrb2 gene are measured and the expression levels of an expression product of the lilrb1 gene are measured by assaying the biological samples.

30. A method of measuring gene expression for a patient in septic shock, comprising:
    obtaining a biological sample taken from the patient in septic shock; and
    assaying the biological sample, including performing a quantitative polymerase chain reaction (PCR) or a quantitative enzyme linked immunosorbent assay (ELISA), to measure an expression level of an expression product expressed from any of (i) a *Homo sapiens* leukocyte immunoglobulin-like receptor, subfamily B with transmembrane domain (TM) and immunoreceptor tyrosine-based inhibition motif (ITIM) domains, member 2 (lilrb2) gene, or (ii) a *Homo sapiens* leukocyte immunoglobulin-like receptor, subfamily B with TM and ITIM domains, member 1 (lilrb1) gene.

31. The method of claim 30, wherein the expression level of the expression product is measured without hybridization on a biochip.

32. The method of claim 30, wherein the biological sample is a blood sample.

33. The method of claim 30, wherein the quantitative PCR is performed.

34. The method of claim 30, wherein the quantitative ELISA is performed.

35. A method of measuring gene expression for a patient in septic shock, comprising:

obtaining a biological sample taken from the patient in septic shock; and assaying the biological sample to measure whether there is overexpression relative to a control level from either a healthy subject or non-surviving septic-shock patient of an expression product expressed from any of (i) a *Homo sapiens* leukocyte immunoglobulin-like receptor, subfamily B with transmembrane domain (TM) and immunoreceptor tyrosine-based inhibition motif (ITIM) domains, member 2 (lilrb2) gene, or (ii) a *Homo sapiens* leukocyte immunoglobulin-like receptor, subfamily B with TM and ITIM domains, member 1 (lilrb1) gene, wherein an expression level of the expression product is measured without hybridization on a biochip.

36. The method of claim 35, wherein assaying the biological sample includes performing a quantitative polymerase chain reaction (PCR).

37. The method of claim 35, wherein assaying the biological sample includes performing a quantitative immunoassay.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: LILRB2 PRIMER 1

<400> SEQUENCE: 1
ccagagccca cagacagagg                                               20

<210> SEQ ID NO 2
<211> LENGTH: 21
<212> TYPE: DNA
<213> ORGANISM: Artificial Sequence
<220> FEATURE:
<223> OTHER INFORMATION: LILRB2 PRIMER 2

<400> SEQUENCE: 2
tgtccttcac ggcagcatag a                                             21

<210> SEQ ID NO 3
<211> LENGTH: 20
<212> TYPE: DNA
<213> ORGANISM: Artificial Sequence
<220> FEATURE:
<223> OTHER INFORMATION: LILRB2 SONDE 3

<400> SEQUENCE: 3
gactccacac tcagtagaag                                               20

<210> SEQ ID NO 4
<211> LENGTH: 20
<212> TYPE: DNA
<213> ORGANISM: Artificial Sequence
<220> FEATURE:
<223> OTHER INFORMATION: HPRT1 PRIMER 4

<400> SEQUENCE: 4
ccaaagatgg tcaaggtcgc                                               20

<210> SEQ ID NO 5
<211> LENGTH: 22
<212> TYPE: DNA
<213> ORGANISM: Artificial Sequence
<220> FEATURE:
<223> OTHER INFORMATION: HPRT1 PRIMER 5

<400> SEQUENCE: 5
gacacaaaca tgattcaaat cc                                            22

<210> SEQ ID NO 6
<211> LENGTH: 23
<212> TYPE: DNA
<213> ORGANISM: Artificial Sequence
<220> FEATURE:
<223> OTHER INFORMATION: HPRT1 SONDE 6

<400> SEQUENCE: 6
caagtttgtt gtaggatatg ccc                                           23
```